United States Patent [19]

Horide et al.

[11] 4,349,379
[45] Sep. 14, 1982

[54] EMULSIFIABLE CONCENTRATE FOR WEED CONTROL

[75] Inventors: Fumio Horide; Kozo Tsuji, both of Osaka; Ryo Yoshida, Kawanishi, all of Japan

[73] Assignee: Sumitomo Chemical Company, Limited, Osaka, Japan

[21] Appl. No.: 210,791

[22] Filed: Nov. 26, 1980

[30] Foreign Application Priority Data

Nov. 26, 1979 [JP] Japan .................. 54-153224

[51] Int. Cl.³ ............................................ A01N 25/02
[52] U.S. Cl. ................................. 71/120; 71/DIG. 1
[58] Field of Search ........................ 71/120, DIG. I

[56] References Cited

U.S. PATENT DOCUMENTS

| | | | |
|---|---|---|---|
| 3,119,682 | 1/1964 | Martin | 71/98 |
| 3,297,425 | 1/1967 | Barbaras | 71/103 |
| 3,373,010 | 3/1968 | Olson | 71/120 |
| 3,681,348 | 8/1972 | McCoy | 71/98 |
| 3,792,996 | 2/1974 | Barron et al. | 71/DIG. I |
| 3,869,276 | 3/1975 | Priola | 71/93 |
| 3,914,308 | 10/1975 | McCoy | 564/277 |
| 3,939,272 | 2/1976 | McCoy | 71/120 |
| 4,044,118 | 8/1977 | McCoy | 71/120 |
| 4,129,436 | 12/1978 | Takemoto et al. | 71/120 |
| 4,174,960 | 11/1979 | Hendrikson | 71/121 |

FOREIGN PATENT DOCUMENTS 718854 2/1963 Canada .

OTHER PUBLICATIONS

Kochmann et al., (Ger. Offen. 2,024,297), Chem. Abst., vol. 75, (1971), 97581z.

*Primary Examiner*—Catherine L. Mills
*Attorney, Agent, or Firm*—Birch, Stewart, Kolasch and Birch

[57] ABSTRACT

An emulsifiable concentrate for weed control, which comprises 10 to 40 parts by weight of N'-[4-(4-methylphenethyloxy)phenyl]-N-methoxy-N-methylurea, 5 to 20 parts by weight of an emulsifier, 5 to 35 parts by weight of at least one of phenolic solvents of the formula:

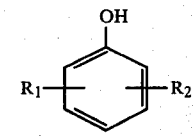

wherein $R_1$ and $R_2$ are each hydrogen or methyl, and 5 to 80 parts by weight of at least one of aromatic hydrocarbon solvents having 6 to 11 carbon atoms.

3 Claims, No Drawings

EMULSIFIABLE CONCENTRATE FOR WEED CONTROL

The present invention relates to an emulsifiable concentrate for weed control. More particularly, it relates to an emulsifiable concentrate for weed control comprising as an active ingredient N'-[4-(4-methylphenethyloxy)phenyl]N-methoxy-N-methylurea (hereinafter referred to as "Compound A").

The purpose of this invention is to provide an emulsifiable concentrate comprising Compound A in a high concentration (i.e. 10–40% by weight), which has a good emulsion stability and an excellent storage stability at low temperature.

Compound A is known to be a herbicide for treatment of soil and foliage, which shows a strong herbicidal activity against a wide variety of weeds and has a selectivity to soybean, rice, corn, peanut, cotton, wheat, etc. (cf. U.S. Pat. No. 4,129,436). Thus, Compound A exerts a strong herbicidal action at a small dose on broad-leaved weeds such as redroot pigweed (*Amaranthus retroflexus*), common lambsquarters (*Chenopodium album*), cocklebur (*Xanthium pennsylvanicum*), annual morningglory (*Ipomoea purpurea*), chickweed (*Stellaria media*), radish (*Raphanus sativus*), pale smartweed (*Polygonum lapathiofolium*), toothcup (*Rotala indica*), pickerelweed (*Monochoria vaginalis*), false pimpernel (*Linderna pyxidaria*), pitchfork (*Bidens frondosa*), black nightshade (*Solanum nigrum*), sunflower (*Helianthus annus*), jimson weed (*Datura stramonium*) and velvetleaf (*Abutilon theopharasti*), Graminae weeds such as goose grass (*Eleusine indica*), large crabgrass (*Digitaria sanguinalis*), barnyard grass (*Echinochloa crus-galli*), green foxtail (*Setaria viridis*) and nutsedge (*Cyperus difformis*), etc.

Compound A is usually employed in the form of emulsifiable concentrate or wettable powder. In general, an emulsifiable concentrate is preferred, because the use of Compound A as an emulsifiable concentrate produces a higher herbicidal activity than the use as a wettable powder, particularly when Gramineae weeds are treated. Since Compound A is somewhat soluble in water-immiscible solvents (e.g. xylene) ordinarily employed for an emulsifiable concentrate at room temperature, an emulsifiable concentrate comprising Compound A in a concentration of 10 to 15% by weight can be easily produced. However, the solubility of Compound A in such solvents at low temperatures (e.g. 0° C.) is small, and the storage stability at low temperatures is poor. Thus, Compound A tends to crystallize out from its emulsifiable concentrate when stored at low temperatures. Because of this reason, a practically available emulsifiable concentrate contains Compound A only in a concentration of about 10% by weight or less. Instead of or in addition to the said ordinary water-immiscible solvents, the use of other water-soluble solvents which can well dissolve Compound A such as dimethylformamide or dimethylsulfoxide may be attempted. However, even from an aqueous dilution of such an emulsifiable concentrate, Compound A is crystallized out within a short period of time. This crystallization causes unfavorable clogging at the openings of the nozzle of a sprayer and further results in deterioration of the herbicidal activity. Thus, the appearance of an emulsifiable concentrate comprising Compound A in a high concentration and still having a high emulsion stability and a storage stability at low temperatures has been highly demanded.

As the result of an extensive study, it has now been found that the use of a certain solvent mixture can provide an emulsifiable concentrate comprising Compound A in a high concentration with a high emulsion stability and a good storage stability at low temperatures.

The emulsifiable concentrate of the present invention comprises 10 to 40 parts by weight of N'-[4-(4-methylphenethyloxy)phenyl]-N-methoxy-N-methylurea, 5 to 20 parts by weight of an emulsifier, 5 to 35 parts by weight of at least one phenolic solvent of the formula:

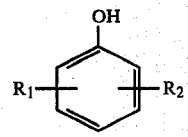

wherein $R_1$ and $R_2$ are each hydrogen or methyl, and 5 to 80 parts by weight at least one of aromatic hydrocarbon solvent having 6 to 11 carbon atoms.

As the emulsifier, there is preferably employed polyoxyethylene alkyl aryl ether sulfate, polyoxyethylene styryl aryl ether sulfate, etc. There is also preferably employed the combination of at least two non-ionic surfactants (e.g. polyoxyethylene alkyl aryl ether, polyoxyethylene styryl aryl ether, polyoxyethylene styryl aryl ether polymer, polyoxyethylene fatty acid ester, sorbitan fatty acid ester, polyoxyethylene sorbitan fatty acid ester) with calcium salts of alkylarylsulfonates. Examples of the emulsifier which is suitable for this invention are commercially available under the trade names "Sorpol 1200" (manufactured by Toho Kagaku K. K.), "Sorpol 2680" (manufactured by Toho Kagaku K. K.), "Sorpol 7290" (manufactured by Toho Kagaku K. K.), "Sorpol 9838" (manufactured by Toho Kagaku K. K.), etc.

Examples of the phenolic solvent are phenol, cresol and xylenol. Any of their isomers are usable alone or in a mixture. Particularly preferred is cresol in liquid at room temperature.

Examples of the aromatic hydrocarbon solvent having 6 to 11 carbon atoms are benzene, toluene, xylene, ethylbenzene, methylethylbenzene, tetramethylbenzene, diethylbenzene, dimethylethylbenzene, trimethylethylbenzene, dimethylpropylbenzene, diethylmethylbenzene, ethylpropylbenzene, methylnaphthalene, etc. These aromatic hydrocarbon solvents may be used in a mixture. For instance, "Solvesso 100" (manufactured by Esso Standard Co.), "Solvesso 150" (manufactured by Esso Standard Co.), "Shellsol A" (manufactured by Shell Oil Co.), "Shellsol AB" (manufactured by Shell Oil Co.), "Tenneco 500/100" (manufactured by Tenneco Oil Co.), etc., which are commercially available mixtures of said aromatic hydrocarbon solvents, can be used as such in the emulsifiable concentrate of the invention.

In the emulsifiable concentrate of the invention, the content of Compound A as the active ingredient is usually from 10 to 40% by weight, preferably from 20 to 30% by weight, based on the weight of the emulsifiable concentrate. The amount of the emulsifier is normally from 5 to 20 parts by weight, favorably from 10 to 15 parts by weight, to 100 parts by weight of the emulsifiable concentrate. The amounts of the phenolic solvent and of the aromatic hydrocarbon solvent are largely dependent upon the content of the active ingredient in the emulsifiable concentrate and may be respectively from 5 to 35 parts by weight and 5 to 80 parts by weight, particularly from 15 to 25 parts by weight and from 30 to 55 parts by weight, to 100 parts by weight of the emulsifiable concentrate.

For preparation of the emulsifiable concentrate of this invention, the said essential components may be mixed together by a conventional mixing procedure. One of the typical procedures comprises dissolving or dispersing the phenolic solvent into the aromatic hydrocarbon solvent, adding Compound A and the emulsifier thereto and stirring the resultant mixture to make a uniform solution. When Compound A is dissolved, endothermic phenomenon may occur, and in such case, heating up to 30°–40° C. is usually favorable. However, this heating is not essential. Further, heating to a higher temperature will cause the unfavorable generation of the solvent vapor. If desired, the obtained solution may be filtered.

In practical use, the emulsifiable concentrate of the invention may be diluted to make an appropriate concentration of the active ingredient, which is varied with the content of the active ingredient, the application mode (e.g. soil treatment, foliage treatment), the application time, etc., and then applied. Usually, it is proper to make a dilution of 100 to 2000 times with water.

Practical and presently preferred embodiments of the present invention are illustratively shown in the following Examples wherein part(s) and % are by weight.

EXAMPLE 1 m-Cresol (28 parts) was dissolved in xylene (17 parts), and Compound A (40 parts) and Sorpol 7290 (15 parts) were added thereto. The resultant mixture was stirred at room temperature to make an emulsifiable concentrate comprising Compound A in a concentration of 40%.

EXAMPLE 2

Cresol (mixture; 21 parts) was dissolved in xylene (39 parts), and Compound A (30 parts) and Sorpol 7290 (10 parts) were added thereto. The resultant mixture was stirred at room temperature to make an emulsifiable concentrate comprising Compound A in a concentration of 30%.

EXAMPLE 3

2,4-Xylenol (27 parts) and Compound A (30 parts) were added to Solvesso 100 (28 parts), and the resulting mixture was stirred at room temperature. Sorpol 1200 (15 parts) was added thereto. The resultant mixture was stirred at room temperature to make an emulsifiable concentrate comprising Compound A in a concentration of 30%.

EXAMPLE 4

Phenol (18 parts) and Compound A (30 parts) were added to Tenneco 500/100 (42 parts), and the resulting mixture was stirred at room temperature. Sorpol 9838 (10 parts) was added thereto. The resultant mixture was stirred at room temperature to make an emulsifiable concentrate comprising Compound A in a concentration of 30%.

EXAMPLE 5

Cresol (mixture; 6 parts) was dissolved in xylene (74 parts), and Compound A (10 parts) and Sorpol 2680 (10 parts) were added thereto. The resultant mixture was stirred at room temperature to make an emulsifiable concentrate comprising Compound A in a concentration of 10%.

EXAMPLE 6

2,5-Xylenol (8 parts) and 3,4-xylenol (8 parts) were dissolved in Shellsol AB (54 parts), and Compound A (20 parts) and Sorpol 7290 (10 parts) were added thereto. The resultant mixture was stirred at room temperature to make an emulsifiable concentrate comprising Compound A in a concentration of 20%.

EXAMPLE 7 o-Cresol (31 parts) was dissolved in Tenneco 500/100 (29 parts), and Compound A (30 parts) and Sorpol 9838 (10 parts) were added thereto. The resultant mixture was stirred at room temperature to make an emulsifiable concentrate comprising Compound A in a concentration of 30%.

COMPARATIVE EXAMPLE 1

Compound A (10 parts), Sorpol 2680 (10 parts) and xylene (80 parts) were mixed together to make an emulsifiable concentrate comprising Compound A in a concentration of 10%.

COMPARATIVE EXAMPLE 2

Compound A (20 parts), Sorpol 2680 (15 parts), xylene (20 parts) and dimethylformamide (45 parts) were mixed together to make an emulsifiable concentrate comprising Compound A in a concentration of 20%.

COMPARATIVE EXAMPLE 3

Compound A (20 parts), Sorpol (15 parts), xylene (20 parts) and dimethylsulfoxide (45 parts) were mixed together to make an emulsifiable concentrate comprising Compound A in a concentration of 20%.

REFERENCE EXAMPLE 1

Compound A (50 parts), 50% hydrated silicone dioxide powder of polyoxyethylene alkyl aryl ether (10 parts), hydrated silica (10 parts) and diatomaceous earth (30 parts) were mixed together and pulverized to make a wettable powder comprising Compound A in a concentration of 50%.

TEST EXAMPLE 1

According to the method as described in CIPAC (Collaborative International Pesticides Analytical Council) MT 39.1, each of the emulsifiable concentrate prepared in Examples 1 to 7 and Comparative Examples 1 to 3 was kept in an incubator of 0° C., and the precipitation of crystals was examined visually.

The results are shown in Table 1.

TABLE 1

|  | After 1 day | After 3 days | After 7 days |
|---|---|---|---|
| Example 1 | — | — | — |
| 2 | — | — | — |
| 3 | — | — | — |
| 4 | — | — | — |
| 5 | — | — | — |
| 6 | — | — | — |
| 7 | — | — | — |
| Comparative Example 1 | + | + | + |
| Comparative Example 2 | — | — | — |

TABLE 1-continued

|  | After 1 day | After 3 days | After 7 days |
|---|---|---|---|
| Comparative Example 3 | — | — | — |

Note:
+, precipitated crystals were observed;
—, precipitated crystals were not observed.

TEST EXAMPLE 2

Each of the emulsifiable concentrate prepared in Examples 1 to 7 and Comparative Examples 1 to 3 was diluted with WHO standard hard water to make a dilution comprising Compound A in a concentration of 3000 ppm at 30° C., and the emulsion stability was examined visually.

The results are shown in Table 2.

TABLE 2

|  | After 30 minutes | After 60 minutes | After 120 minutes |
|---|---|---|---|
| Example 1 | A | A | B |
| 2 | A | A | A |
| 3 | A | A | B |
| 4 | A | A | A |
| 5 | A | A | B |
| 6 | A | A | B |
| 7 | A | A | C |
| Comparative Example 1 | A | A | A |
| Comparative Example 2 | D | E | E |
| Comparative Example 3 | D | E | E |

Note:
A, stable;
B, the amount of precipitated crystals was extremely trace;
C, the amount of precipitated crystals was trace;
D, the amount of precipitated crystals was small;
E, the amount of precipitated crystals was considerable.

TEST EXAMPLE 3

Into a plastic tray of 35 cm×25 cm×10 cm (high), field soil was filled, and the seeds of soybean, morning-glory (*Ipomoea purpurea*), cocklebur (*Xanthium chinese*), velvetleaf (*Abutilon theophrasti*) and large crabgrass (*Digitaria sanguinalis*) were sowed and cultivated in a greenhouse for 3 weeks. A designed amount of the emulsifiable concentrate as prepared in any of Examples 1 to 7 and Comparative Example 2 or of the wettable powder as prepared in Reference Example 1 was diluted with water to make a volume of 5 liters per are, and the dilution was applied over the top of the plants by the aid of a small sprayer for foliar treatment. After cultivation in the greenhouse for additional 3 weeks, the remaining terrestrial parts of the plants was measured, and the percentage of the measured weight in the treated plot to the measured weight in the untreated plot was calculated. The phytotoxicity and the herbicidal activity were evaluated on the following criteria:

| Evaluated value | Fresh weight (percentage to untreated plot) | |
|---|---|---|
|  | Soybean | Weeds |
| 5 | 0–39 | 0 |
| 4 | 40–59 | 1–10 |
| 3 | 60–79 | 11–20 |
| 2 | 80–89 | 21–40 |
| 1 | 90–99 | 41–60 |
| 0 | 100 | 61–100 |

The results are shown in Table 3.

TABLE 3

| | Dose of Compound A (g/are) | Soybean | Weeds | | | |
|---|---|---|---|---|---|---|
| | | | Morning-glory | Cocklebur | Velvetleaf | Large crabgrass |
| Example 1 | 10 | 0 | 5 | 5 | 5 | 5 |
| | 5 | 0 | 5 | 5 | 5 | 4 |
| | 2.5 | 0 | 4 | 5 | 5 | 3 |
| Example 2 | 10 | 0 | 5 | 5 | 5 | 4 |
| | 5 | 0 | 5 | 5 | 5 | 4 |
| | 2.5 | 0 | 4 | 5 | 4 | 3 |
| Example 3 | 10 | 0 | 5 | 5 | 5 | 4 |
| | 5 | 0 | 5 | 5 | 5 | 4 |
| | 2.5 | 0 | 4 | 5 | 4 | 3 |
| Example 4 | 10 | 0 | 5 | 5 | 5 | 5 |
| | 5 | 0 | 5 | 5 | 5 | 4 |
| | 2.5 | 0 | 5 | 5 | 4 | 3 |
| Example 5 | 10 | 0 | 5 | 5 | 5 | 4 |
| | 5 | 0 | 5 | 5 | 5 | 4 |
| | 2.5 | 0 | 4 | 5 | 4 | 3 |
| Example 6 | 10 | 0 | 5 | 5 | 5 | 4 |
| | 5 | 0 | 5 | 5 | 4 | 4 |
| | 2.5 | 0 | 4 | 5 | 4 | 3 |
| Example 7 | 10 | 0 | 5 | 5 | 5 | 5 |
| | 5 | 0 | 4 | 5 | 5 | 4 |
| | 2.5 | 0 | 4 | 4 | 4 | 3 |
| Comparative Example 2 | 10 | 0 | 4 | 5 | 4 | 3 |
| | 5 | 0 | 3 | 4 | 3 | 3 |
| | 2.5 | 0 | 3 | 3 | 3 | 2 |
| Reference Example 1 (Wettable powder) | 10 | 0 | 5 | 5 | 5 | 3 |
| | 5 | 0 | 4 | 5 | 5 | 2 |
| | 2.5 | 0 | 3 | 4 | 4 | 1 |

As understood from the results in Test Example 1, the emulsifiable concentrate of Comparative Example 1 is inferior in the storage stability at low temperatures. As understood from the results in Test Example 2, the emulsifiable concentrates of Comparative Examples 2 and 3 are not practical in the emulsion stability. On the contrary, the emulsifiable concentrates of Examples 1 to 7 have practically satisfactory emulsion stability and storage stability at low temperatures and exhibit sufficiently high herbicidal potency.

What is claimed is:

1. An emulsifiable concentrate for weed control, which comprises 10 to 40 parts by weight of N'-[4-(4-methylphenethyloxy)phenyl]-N-methoxy-N-methylurea, 5 to 20 parts by weight of an emulsifier, 5 to 35 parts by weight of at least one phenolic solvent of the formula:

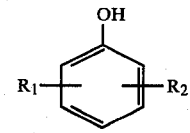

wherein $R_1$ and $R_2$ are each hydrogen or methyl, and 5 to 80 parts by weight of at least one aromatic hydrocarbon solvent having 6 to 11 carbon atoms.

2. The emulsifiable concentrate according to claim 1, which comprises 20 to 30 parts by weight of N'-[4-(4-methylphenethyloxy)phenyl]-N-methoxy-N-methylurea, 10 to 15 parts by weight of the emulsifier, 15 to 25 parts by weight of the phenolic solvent(s) and 30 to 55 parts by weight of the aromatic hydrocarbon solvent(s).

3. The emulsifiable concentrate according to claim 1, wherein the emulsifier is polyoxyethylene alkyl aryl ester sulfate or polyoxyethylene styryl aryl ether sulfate, the phenolic solvent is cresol and the aromatic hydrocarbon solvent is xylene.

* * * * *